US009056109B2

(12) United States Patent
Shi

(10) Patent No.: US 9,056,109 B2
(45) Date of Patent: Jun. 16, 2015

(54) COMPOUNDS AND METHODS FOR TREATING MULTIPLE SCLEROSIS

(75) Inventor: Riyi Shi, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/884,493

(22) PCT Filed: Nov. 10, 2011

(86) PCT No.: PCT/US2011/060110
§ 371 (c)(1),
(2), (4) Date: May 9, 2013

(87) PCT Pub. No.: WO2012/064923
PCT Pub. Date: May 18, 2012

(65) Prior Publication Data
US 2013/0231343 A1    Sep. 5, 2013

Related U.S. Application Data

(60) Provisional application No. 61/412,217, filed on Nov. 10, 2010.

(51) Int. Cl.
*A61K 31/50* (2006.01)
*A61K 31/501* (2006.01)
*A61K 31/502* (2006.01)
*A61K 31/137* (2006.01)

(52) U.S. Cl.
CPC .............. *A61K 31/502* (2013.01); *A61K 31/50* (2013.01); *A61K 31/137* (2013.01)

(58) Field of Classification Search
CPC .... A61K 31/137; A61K 31/50; A61K 31/502
USPC ........... 514/247, 248, 252.01, 252.03, 252.04
See application file for complete search history.

(56) References Cited

U.S. PATENT DOCUMENTS 5,627,165 A     5/1997  Glazier
2007/0232586 A1  10/2007  Ohmoto et al.

FOREIGN PATENT DOCUMENTS

WO    WO2007/127474      11/2007
WO    WO2010015870 A1 *  2/2010  ............ A61K 31/502

OTHER PUBLICATIONS

Hamann et al., "Hydralazine inhibits compression and acrolein-mediated injuries in ex vivo spinal cord", Feb. 2008, Journal of Neurochemistry, vol. 104, Issue 3, pp. 708-718.*
PCT Search Report and Written Opinion for PCT/US2011/060110, completed Jun. 1, 2012.
Liu, Zhuqing, et al., "Design, Synthesis and Biological Evaluation of a Library of Thiocarbazates and their Activity as Cysteine Protease Inhibitors", May 2010, Comb Chem High Throughput Screen, vol. 13, No. 4, pp. 337-351.
Adams JD, Jr., Klaidman LK (1993) Acrolein-induced oxygen radical formation. Free Radical Biology & Medicine 15:187-193.
Burcham PC, Pyke SM (2006) Hydralazine inhibits rapid acrolein-induced protein oligomerization: role of aldehyde scavenging and adduct trapping in cross-link blocking and cytoprotection. Mol Pharmacol 69:1056-1065.
Burcham PC, Kaminskas LM, Fontaine FR, Petersen DR, Pyke SM (2002) Aldehyde-sequestering drugs: tools for studying protein damage by lipid peroxidation products. Toxicology 181-182:229-236.
Burcham PC, Fontaine FR, Kaminskas LM, Petersen DR, Pyke SM (2004) Protein adduct-trapping by hydrazinophthalazine drugs: mechanisms of cytoprotection against acrolein-mediated toxicity. Mol Pharmacol 65:655-664.
Compston A, Coles A (2008) Multiple sclerosis. Lancet 372:1502-1517.
Esterbauer H, Schaur RJ, Zollner H (1991) Chemistry and biochemistry of 4-20 hydroxynonenal, malonaldehyde and related aldehydes. Free Radical Biology & Medicine 11:81-128.
Ghilarducci DP, Tjeerdema RS (1995) Fate and effects of acrolein. Rev Environ Con tarn Toxicol 144:95-146.
Gilgun-Sherki Y, Melamed E, Offen D (2004) The role of oxidative stress in the 25 pathogenesis of multiple sclerosis: the need for effective antioxidant therapy. J Neurol 251:261-268.
Gold R, Linington C, Lassmann H (2006) Understanding pathogenesis and therapy of multiple sclerosis via animal models: 70 years of merits and culprits in experimental autoimmune encephalomyelitis research. Brain 129:1953-1971.
Uchida K, Kanematsu M, Morimitsu Y, Osawa T, Noguchi N, Niki E (1998a) 30 Acrolein is a product of lipid peroxidation reaction. Formation of free acrolein and its conjugate with lysine residues in oxidized low density lipoproteins. J Biol Chem 273:16058-16066.
Hamann K, Shi R (2009) Acrolein scavenging: a potential novel mechanism of attenuating oxidative stress following spinal cord injury. J Neurochem 111:1348-1356.
Hamann K, Durkes A, Ouyang H, Uchida K, Pond A, Shi R (2008b) Critical role 5 of acrolein in secondary injury following ex vivo spinal cord trauma. J Neurochem 107:712-721.
Kalyvas A, David S (2004) Cytosolic phospholipase A2 plays a key role in the pathogenesis of multiple sclerosis-like disease. Neuron 41:323-335.
Kaminskas LM, Pyke SM, Burcham PC (2004a) Reactivity of 10 hydrazinophthalazine drugs with the lipid peroxidation products acrolein and crotonaldehyde. Org Biomol Chem 2:2578-2584.
Kaminskas LM, Pyke SM, Burcham PC (2004b) Strong protein adduct trapping accompanies abolition of acrolein mediated hepatotoxicity by hydralazine in mice. J Pharmacol Exp Ther 310:1003-1010.
Kehrer JP, Biswal SS (2000) The molecular effects of acrolein. Toxicological Sciences 57:6-15.
Liu-Snyder P, McNally H, Shi R, Borgens RB (2006) Acrolein-mediated mechanisms of neuronal death. J Neurosci Res 84:209-218.
Lovell MA, Xie C, Markesbery WR (2001) Acrolein is increased in Alzheimer's 20 disease brain and is toxic to primary hippocampal cultures. Neurobiology of Aging 22:187-194.

(Continued)

*Primary Examiner* — My-Chau T Tran
(74) *Attorney, Agent, or Firm* — Brown Rudnick LLP; Adam M. Schoen

(57) ABSTRACT

The invention described herein pertains to the treatment of multiple sclerosis. In particular, the invention described herein pertains to the treatment of multiple sclerosis using compounds that modulate the action of acrolein.

29 Claims, 6 Drawing Sheets

(56) References Cited

OTHER PUBLICATIONS

Luo J, Shi R (2004) Acrolein induces axolemmal disruption, oxidative stress, and mitochondrial impairment in spinal cord tissue. Neurochemsitry International 44:475-486.

Luo J, Shi R (2005) Acrolein induces oxidative stress in brain mitochondria. Neurochem Int 46:243-252.

Luo J, Uchida K, Shi R (2005a) Accumulation of acrolein-protein adducts after traumatic spinal cord injury. Neurochem Res. 30:291-295.

Luo J., Robinson, JP, Shi, R. (2005b) Acrolein-induced cell death in PC 12 Cells: role of mitchondria-mediated oxidative stress. Neurochem Int. 47: 449-457.

Montine TJ, Neely MD, Quinn JF, Beal MF, Markesbery WR, Roberts LJ, 30 Morrow JD (2002) Lipid peroxidation in aging brain and Alzheimer's disease. Free Radic Biol Med 33:620-626.

Wood PL, Khan MA, Moskal JR, Todd KG, Tanay YA, Baker G (2006) Aldehyde load in ischemia-reperfusion brain injury: neuroprotection by neutralization of reactive aldehydes with phenelzine. Brain Res 1122:184-190.

Uchida K, Kanematsu M. Sakai K, Matsuda T, Hattori N, Mizuno Y, Suzuki D, Miyata T, Noguchi N, Niki E, Osawa T (1998b) Protein-bound acrolein: potential markers for oxidative stress. Proceedings of the National Academy of Sciences of the United States of 35 America 95:4882-4887.

Shao B, O'Brien K D, McDonald TO, Fu X, Oram JF, Uchida K, Heinecke JW (2005a) Acrolein modifies apolipoprotein A-I in the human artery wall. Ann N Y Acad Sci 1043:396-403.

Shao B, Fu X, McDonald TO, Green PS, Uchida K, O'Brien KD, Oram JF, 5 Heinecke JW (2005b) Acrolein impairs ATP binding cassette transporter AI-dependent cholesterol export from cells through site-specific modification of apolipoprotein A-T. J Biol Chem 280:36386-36396.

Shao C, Roberts KN, Markesbery WR, Scheff SW, Lovell MA (2006) Oxidative stress in head trauma in aging. Free Radic Biol Med. 41:77-85.

Shi R, Luo J, Peasley MA (2002) Acrolein Inflicts axonal membrane dispruption and conduction loss in isolated guinea pig spinal cord. Neuroscience 115:337-340.

Shibata N, Nagai R, Miyata S, Jono T, Horiuchi S, Hirano A, Kato S, Sasaki S, Asayama K, Kobayashi M (2000) Nonoxidative protein glycation is implicated in familial amyotrophic lateral sclerosis with superoxide dismutase-1 mutation. Acta Neuropathol (Berl) 15 100:275-284.

Shields DC, banik NT (1999) Patolphysiological role of calpain in experimental demyelination. J Neurosci Res 55:533-541.

Shields DC, Schaecher KE, Saido TC, Banik NL (1999) A putative mechanism of demyelination in multiple sclerosis by a proteolytic enzyme, calpain. Proc Natl Acad Sci U S A 96:11486-11491.

Smith KJ, Kapoor R, Felts PA (1999) Demyelination: the role of reactive oxygen and nitrogen species. Brain Pathol 9:69-92.

Trapp BD, Nave KA (2008) Multiple sclerosis: an immune or neurodegenerative disorder? Annu Rev Neurosci 31:247-269.

Trapp BD, Ransohoff R, Rudick R (1999) Axonal pathology in multiple sclerosis: relationship to neurologic disability. Curr Opin Neurol 12:295-302.

Trapp BD, Peterson J, Ransohoff RM, Rudick R, Mork S, Bo L (1998) Axonal transection in the lesions of multiple sclerosis. N Engl J Med 338:278-285.

Burcham, et al. (2000) The antihypertensive hydralazine is an efficient scavenger of acrolein, Redox, 5: 47-49.

\* cited by examiner

COMPOUNDS AND METHODS FOR TREATING MULTIPLE SCLEROSIS

CROSS REFERENCE TO RELATED APPLICATIONS

This application is a national stage entry under 35 USC §371(b) of International Application No. PCT/US2011/060110, filed Nov. 10, 2011, which claims priority under 35 U.S.C. §119(e) to U.S. Provisional Application No. 61/412,217, filed Nov. 10, 2010, which is expressly incorporated by reference herein.

TECHNICAL FIELD

The invention described herein pertains to the treatment of multiple sclerosis. In particular, the invention described herein pertains to the treatment of multiple sclerosis using compounds that modulate the action of acrolein.

BACKGROUND AND SUMMARY OF THE INVENTION

Multiple sclerosis (MS) is a severely debilitating neurodegenerative disease marked by progressive demyelination and functional loss in the central nervous system (CNS) (Gold et al., 2006; Compston and Coles, 2008). Oxidative stress resulting from inflammation is known to play a critical role in demyelination, a major pathology in MS (Smith et al., 1999; Gilgun-Sherki et al., 2004). However, conventional free radical scavengers have been unsuccessful at preventing disease development or progression (Smith et al., 1999; Gold et al., 2006; Compston and Coles, 2008). Hence, a priority in MS research is to improve understanding of the mechanisms of oxidative stress and thereby identify novel, more effective therapeutic targets.

It has been discovered that in vivo production of acrolein may mediate the initiation and/or progression of multiple sclerosis. It has also been discovered herein that compounds capable of interacting with acrolein are efficacious in treating multiple sclerosis. Without being bound by theory, it is believed herein that compounds that are capable of scavenging and/or preventing acrolein from contacting tissues are efficacious in treating multiple sclerosis.

Acrolein, a reactive α,β-unsaturated aldehyde, has been reported to be a product of oxidative stress and lipid peroxidation. Furthermore, acrolein has been reported to remain active in the body for several days (Ghilarducci and Tjeerdema, 1995) while more commonly studied oxidative species decay within seconds (Halliwell and Gutteridge, 1999). Therefore, and without being bound by theory, it is believed herein that acrolein may be a key factor in perpetuating oxidative stress and may cause progressive myelin damage and functional loss. Accordingly, acrolein may be a potential novel target for MS therapeutics.

Described herein is the role of acrolein in the pathogenesis of MS using a well-established animal model of MS. Experimental autoimmune encephalomyelitis (EAE) was induced in mice, and acrolein levels were determined in control and experimental groups.

It has also been discovered that hydrazinopyridazines, fused hydrazinopyridazines, phenylethylhydrazines, and combinations thereof are useful in treating multiple sclerosis.

In one illustrative embodiment of the invention, compounds of the following formula are described herein:

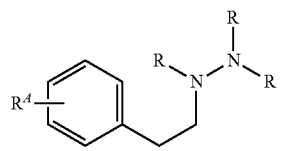

and pharmaceutically acceptable salts thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In one illustrative embodiment of the invention, compounds of the following formula are described herein:

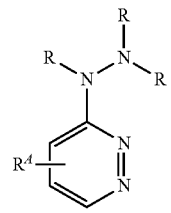

and pharmaceutically acceptable salts thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, pharmaceutical compositions containing one or more of the compounds are also described herein. In one aspect, the compositions include a therapeutically effective amount of the one or more compounds for treating a patient with MS. It is to be understood that the compositions may include other components and/or ingredients, including, but not limited to, other therapeutically active compounds, and/or one or more carriers, diluents, excipients, and the like.

It is appreciated herein that the compounds described herein may be used alone or in combination with other compounds useful for treating MS, including those compounds that may be therapeutically effective by the same or different modes of action. In addition, it is appreciated herein that the compounds described herein may be used in combination with other compounds that are administered to treat other symptoms of MS.

In another embodiment, methods for using the compounds and pharmaceutical compositions for treating patients with MS are also described herein. In one aspect, the methods include the step of administering one or more of the compounds and/or compositions described herein to a patient with MS. In another aspect, the methods include administering a therapeutically effective amount of the one or more compounds and/or compositions described herein for treating patients with MS. In another embodiment, uses of the compounds and compositions in the manufacture of a medicament for treating patients with MS are also described herein. In one aspect, the medicaments include a therapeutically effective amount of the one or more compounds and/or compositions for treating a patient with MS. In another embodiment, unit doses and/or unit dosage forms that include the compounds and pharmaceutical compositions for treating patients with MS are also described herein. In another aspect, the unit doses and/or unit dosage forms are administered to a patient with MS.

In another embodiment, compounds, compositions, methods, and uses are described herein for treating progressive forms of MS. In another embodiment, compounds compositions, methods, and uses are described herein for treating relapsing forms of MS.

In another embodiment, compounds, compositions, methods, and uses are described herein for treating early, mid, and/or late stage MS. In another embodiment, compounds, compositions, methods, and uses are described herein for prophylactically treating MS. It has been discovered herein that the compounds, compositions, methods, and uses described herein are effective in treating MS both before and after symptoms are observed. Illustratively, prophylactic treatment may be performed in patients who are at an increased risk of developing MS, such as patients having a history of relapsing MS, patients having a family history or relative with MS, and the like. Illustratively, prophylactic treatment may be performed in patients who do not have outwardly observable symptoms of the MS, but who show early damage to myelin, slow or inadequate myelin repair, high levels of acrolein, and the like. It has also been discovered herein that beginning treatment using the compounds, compositions, methods, and uses described herein earlier in the disease progression of MS may lead to better patient outcomes, such as but not limited to delayed onset of outwardly observable symptoms or more severe symptoms, overall improved amelioration of symptoms, and the like.

DETAILED DESCRIPTION

Figure 1:
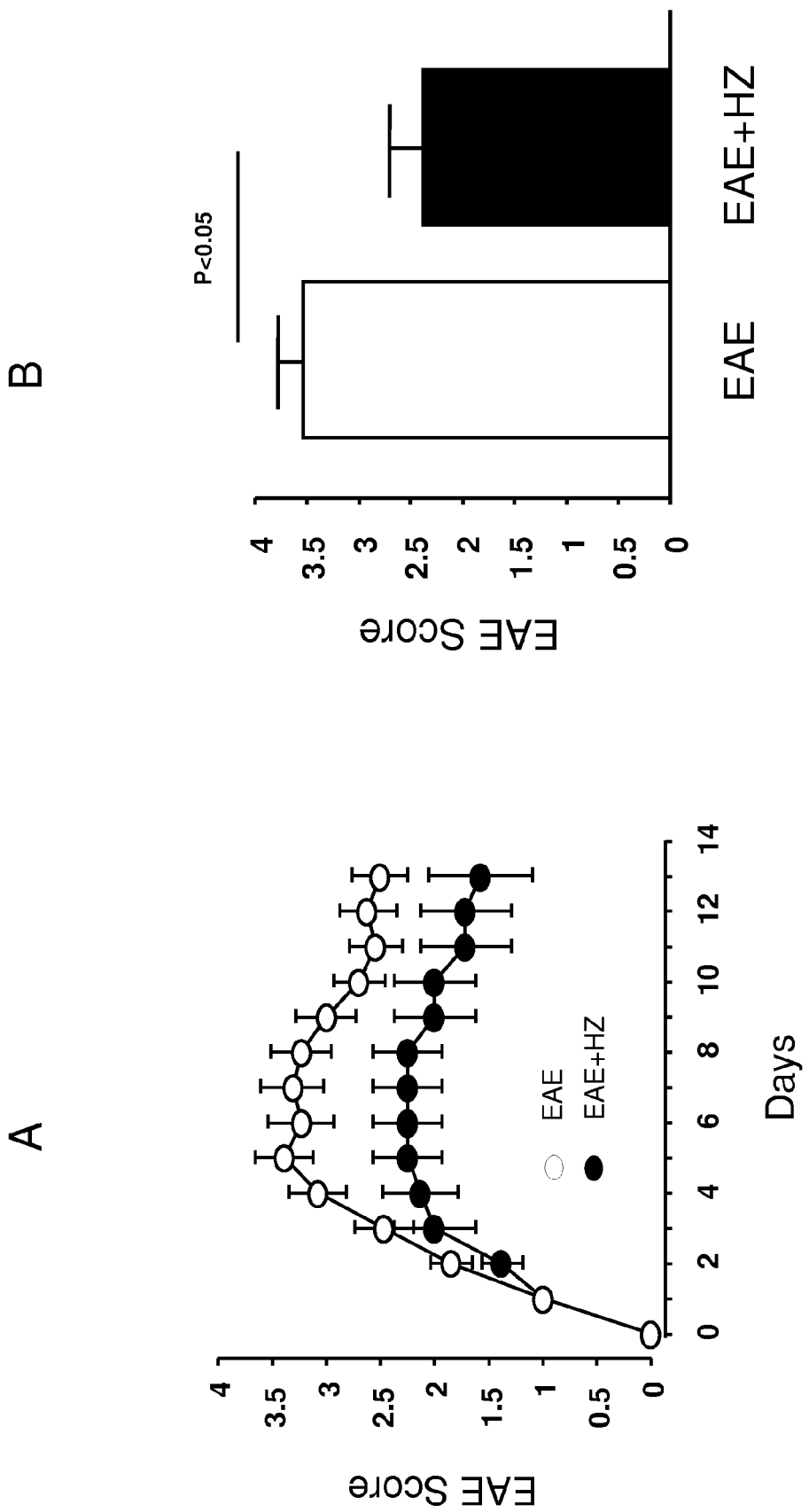
FIG. 1A shows the behavioral scores evaluated daily on a 5 point scale for mice in sham treated (EAE) and hydralazine treated (EAE+HZ) groups.
FIG. 1B shows a comparison of the highest scores for each mouse averaged within the group.

In one embodiment, described herein is a method for treating a patient with multiple sclerosis, the method comprising the step of administering to the patient a therapeutically effective amount of one or more hydrazinopyridazines, fused hydrazinopyridazines, phenylethylhydrazines, or combinations thereof.

In another embodiment, described herein is a method wherein the phenylethylhydrazine is a compound of the formula

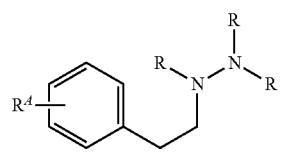

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a method wherein the hydrazinopyridazine or fused hydrazinopyridazine is a compound of the formula

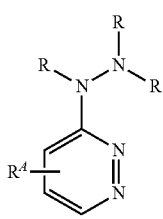

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a pharmaceutical composition, unit dose, or unit dosage form for treating a patient with multiple sclerosis, the method comprising the step of administering to the patient a therapeutically effective amount of one or more hydrazinopyridazines, fused hydrazinopyridazines, phenylethylhydrazines, or combinations thereof.

In another embodiment, described herein is a pharmaceutical composition, unit dose, or unit dosage form wherein the phenylethylhydrazine is a compound of the formula

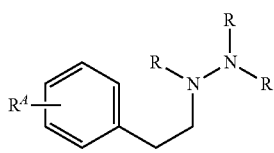

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a pharmaceutical composition, unit dose, or unit dosage form wherein the hydrazinopyridazine or fused hydrazinopyridazine is a compound of the formula

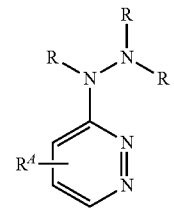

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

In another embodiment, described herein is a method, use, pharmaceutical composition, unit dose, or unit dosage form as described above wherein $R^A$ represents three hydrogens.

In another embodiment, described herein is a method, use, pharmaceutical composition, unit dose, or unit dosage form as described above $R^A$ includes an optionally substituted benzo group.

In another embodiment, described herein is a method, use, pharmaceutical composition, unit dose, or unit dosage form as described above $R^A$ includes an optionally substituted fused piperidine.

In another embodiment, described herein is a method, use, pharmaceutical composition, unit dose, or unit dosage form as described above $R^A$ includes a hydrazino or derivative thereof.

In another embodiment, described herein is a method, use, pharmaceutical composition, unit dose, or unit dosage form as described above $R^A$ includes a hydrazino.

In another embodiment, described herein is a method, use, pharmaceutical composition, unit dose, or unit dosage form as described above $R^A$ includes amino or a derivative thereof.

In another embodiment, described herein is a method, use, pharmaceutical composition, unit dose, or unit dosage form as described above $R^A$ includes dialkylamino, where each alkyl is independently selected, and independently optionally substituted.

In another embodiment, described herein is a method, use, pharmaceutical composition, unit dose, or unit dosage form as described above each R is hydrogen.

In another embodiment, described herein is a method, use, pharmaceutical composition, unit dose, or unit dosage form as described above at least one R is acyl.

In another embodiment, described herein is a method, use, pharmaceutical composition, unit dose, or unit dosage form as described above at least one R is optionally substituted alkoxycarbonyl.

In another embodiment, described herein is a method, use, pharmaceutical composition, unit dose, or unit dosage form as described above the one or more compounds are selected from the group consisting of hydralazine, cadralazine, dihydralazine, endralazine, phenelzine, and pharmaceutically acceptable salts of the foregoing, and combinations thereof.

In another embodiment, described herein is a method, use, pharmaceutical composition, unit dose, or unit dosage form as described above the one or more compounds are selected from the group consisting of hydralazine, dihydralazine, endralazine, and pharmaceutically acceptable salts of the foregoing, and combinations thereof.

In another embodiment, described herein is a method, use, pharmaceutical composition, unit dose, or unit dosage form as described above the one or more compounds are selected from the group consisting of hydralazine, dihydralazine, and pharmaceutically acceptable salts of the foregoing, and combinations thereof.

In another embodiment, described herein is a method, use, pharmaceutical composition, unit dose, or unit dosage form as described above the one or more compounds are selected from the group consisting of phenelzine and pharmaceutically acceptable salts thereof.

Illustratively, hydralazine, a fused hydrazinopyridazine, is a compound that may be included in the pharmaceutical compositions, unit dosage forms, methods, and uses described herein. It has been discovered herein that acrolein is significantly increased as a symptom of MS. It has also been discovered herein that the compounds and compositions described herein, such as hydralazine, phenelzine, and the like, are effective acrolein scavengers and may be used to trap acrolein in a patient with MS. It has been observed herein that acrolein is significantly increased when the behavioral deficits emerge in EAE mice. Illustratively, hydralazine, phenelzine, and like treatments are efficacious in alleviating and/or reducing the MS motor deficits observed in MS patients, may also be accompanied by anatomical improvements, and may lower acrolein levels in spinal cord tissue. Without being bound by theory, it is believed herein that the ability of the compounds like hydralazine and phenelzine to treat MS is due at least in part to the capability of interacting with, blocking, or otherwise intervening in the pathology of acrolein in vivo.

Illustrative hydrazinopyridazines and fused hydrazinopyridazines useful in the methods, uses, formulations, and unit dosage forms described herein are of the formulae

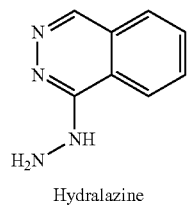

Hydralazine

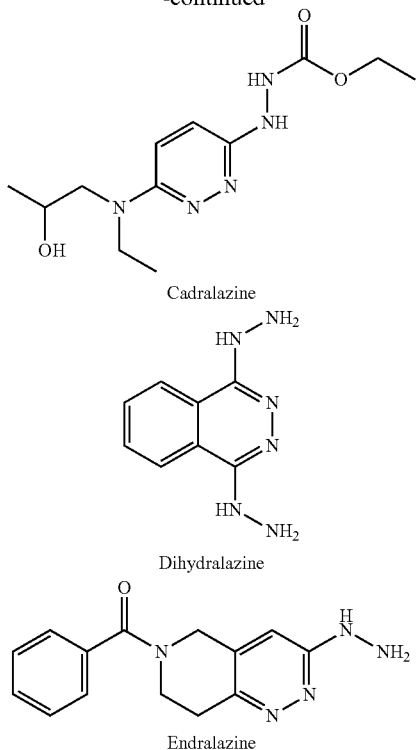

Cadralazine

Dihydralazine

Endralazine and pharmaceutically acceptable salts thereof, and analogs and derivatives of the foregoing.

In another embodiment, the method or unit dose includes a therapeutically effective amount of one or more compounds described herein that is not therapeutically effective or clinically effective for treating hypertension. In another embodiment, the method or unit dose includes a therapeutically effective amount of one or more compounds described herein that is at least about 2-fold, at least about 3-fold, at least about 4-fold, or at least about 5-fold lower than the therapeutically effective or clinically effective dose for treating hypertension. In another embodiment, the method or unit dose includes a therapeutically effective amount of one or more compounds described herein that is at least about 10-fold, at least about 20-fold, at least about 30-fold, or at least about 50-fold lower than the therapeutically effective or clinically effective dose for treating hypertension. In another embodiment, the method or unit dose includes a therapeutically effective amount of one or more compounds described herein that is does not cause, or substantially cause, hypotension.

In another embodiment, the method or unit dose includes a therapeutically effective amount of one or more compounds described herein that is not therapeutically effective or clinically effective for treating depression or anxiety. In another embodiment, the method or unit dose includes a therapeutically effective amount of one or more compounds described herein that is at least about 2-fold, at least about 3-fold, at least about 4-fold, or at least about 5-fold lower than the therapeutically effective or clinically effective dose for treating depression or anxiety. In another embodiment, the method or unit dose includes a therapeutically effective amount of one or more compounds described herein that is at least about 10-fold, at least about 20-fold, at least about 30-fold, or at least about 50-fold lower than the therapeutically effective or clinically effective dose for treating depression or anxiety.

In another embodiment, the compositions, methods, and uses include a therapeutically effective amount of one or more compounds described herein, such as the equivalent of about 0.01 mg/kg to about 2 mg/kg, about 0.01 mg/kg to about 1.5 mg/kg, about 0.01 mg/kg to about 1 mg/kg, or about 0.01 mg/kg to about 0.5 mg/kg, administered orally.

In another embodiment, the compositions, methods, and uses include a therapeutically effective amount of one or more compounds described herein, such as the equivalent of about 0.05 mg/kg to about 2 mg/kg, about 0.05 mg/kg to about 1.5 mg/kg, about 0.05 mg/kg to about 1 mg/kg, or about 0.05 mg/kg to about 0.5 mg/kg, administered orally.

In another embodiment, the compositions, methods, and uses include a therapeutically effective amount of one or more compounds described herein, such as the equivalent of about 0.1 mg/kg to about 2 mg/kg, about 0.1 mg/kg to about 1.5 mg/kg, about 0.1 about 0.1 mg/kg to about 1 mg/kg, or about 0.1 mg/kg to about 0.5 mg/kg, administered orally.

In another embodiment, the compositions, methods, and uses include a therapeutically effective amount of one or more compounds described herein, such as the equivalent of about 0.5 mg/kg to about 5 mg/kg, about 0.5 mg/kg to about 3 mg/kg, about 0.5 mg/kg to about 2 mg/kg, about 0.5 mg/kg to about 1 mg/kg, administered orally.

In each of the foregoing embodiments, it is to be understood that the dose may be single or divided. In addition, it is to be understood that the therapeutically effective amount be administered following any of a wide variety of dosing schedules, including q.d., b.i.d., three times daily, four times daily, and the like.

Accordingly, an illustrative dosing schedule for an adult of average weight may be about 5 mg to 15 mg, p.o. twice, thrice, or four times daily, or about 5 mg to about 10 mg, p.o. twice, thrice, or four times daily.

In another embodiment, described herein are packages for daily administration of one or more compounds or compositions described herein according to the methods or uses described herein, including a unit dosage form as described above wherein the unit dosage form is a single or divided daily dose that sums to a daily amount of about 1 mg to about 50 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 40 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 30 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 25 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 20 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 15 mg of the compound, administered orally.

In another embodiment, described herein are packages for daily administration of one or more compounds or compositions described herein according to the methods or uses described herein, including a unit dosage form is a single or divided daily dose that sums to a daily amount of about 1 mg to about 10 mg of the compound, administered orally.

It is to be understood that other routes of administration may be used, including buccal, sublingual, parenteral, and the like. It is appreciated herein that when other routes of administration that lead to higher bioavailability are used, the illustrative oral doses described herein will be reduced accordingly.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In another embodiment, described herein are pharmaceutical compositions, unit doses, and unit dosage forms as described above further comprising one or more carriers, diluents, or excipients, or a combination thereof.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

In another embodiment, described herein is a method for treating a patient with multiple sclerosis, the method comprising the step of administering to the patient a therapeutically effective amount of one or more compounds, as described herein, capable of blocking or decreasing the action of acrolein on myelin or on axons.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

As used herein, the terms hydrazinopyridazines, fused hydrazinopyridazines, and phenylethylhydrazines generally refer to the compounds described herein and analogs and derivatives thereof, but are not limited to those compounds. Other compounds that are hydrazinopyridazines, fused hydrazinopyridazines, and phenylethylhydrazines are also useful in the methods, uses, pharmaceutical compositions, formulations, and unit dosage forms described herein. It is also to be understood that in each of the foregoing, any corresponding pharmaceutically acceptable salt is also included in the illustrative embodiments described herein.

Illustrative derivatives include, but are not limited to, both those compounds that may be synthetically prepared from the compounds described herein, as well as those compounds that may be prepared in a similar way as those described herein, but differing in the selection of starting materials. For example, it is to be understood that derivatives of those compounds also include the compounds having for example different functional groups on aromatic rings than those explicitly set forth in the compound genera described herein. In addition, it is to be understood that derivatives of those compounds also include the compounds having those same or different functional groups at different positions on the aromatic ring.

It is to be understood that such derivatives may include prodrugs of the compounds described herein, compounds described herein that include one or more protection or protecting groups, including compounds that are used in the preparation of other compounds described herein.

Illustrative analogs include, but are not limited to, those compounds that share functional and in some cases structural similarity to those compounds described herein. For example, described herein are compounds that include a benzopyridazine ring system. Illustrative analogs include, but are not limited to, the corresponding ring expanded or ring contracted compounds, and the like. Other illustrative analogs include, but are not limited to, the corresponding ring systems that include additional heteroatoms, or where the ring fusion is made at a different pair of atoms, and the like.

In addition, as used herein the terms hydrazinopyridazines, fused hydrazinopyridazines, and phenylethylhydrazines also refer to prodrug derivatives of the compounds described herein, and including prodrugs of the various analogs and derivatives thereof. In addition, as used herein, the terms hydrazinopyridazines, fused hydrazinopyridazines, and phenylethylhydrazines also refer to both the amorphous as well as any and all morphological forms of each of the compounds described herein. In addition, as used herein, the terms hydrazinopyridazines, fused hydrazinopyridazines, and phenylethylhydrazines also refer to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein. For example, in another embodiment, when each R is hydrogen, $R^A$ includes an optionally substituted benzo group; or when at least one R is acyl, $R^A$ includes a hydrazine; or when at least one R is acyl, $R^A$ includes an optionally substituted benzo group; and the like.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

The effective use of the compounds, compositions, and methods described herein for treating or ameliorating one or more effects of MS using one or more compounds described herein may be based upon animal models, such as murine, canine, porcine, and non-human primate animal models of disease. For example, it is understood that MS in humans may be characterized by a loss of function, and/or the development of symptoms, each of which may be elicited in animals, such as mice, and other surrogate test animals. In particular the mouse EAE model may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to are to limit invention.

EXAMPLES

Example

Animals

C57BL/6 female mice (8 weeks old) were purchased from Harlan Laboratories and were maintained in the lab animal housing facilities. These studies were performed in compliance with the Purdue Animal Care and Use Committee protocol guidelines at Purdue University, West Lafayette, Ind.

Example

Induction of EAE

Nine-twelve week old mice were subcutaneously injected with 0.1 mL $MOG_{35-55}$/CFA emulsion (EK-0115, Hooke Laboratories) in the neck and lower back (total of 0.2 mL). Within two hours of the injection, 0.1 mL pertussis toxin (EK-0115, Hooke Laboratories) was administered intraperitoneally. A second dose of pertussis toxin of the same volume was given 22-26 hours later. The behavioral performance was assessed using a well established 5-point behavioral scoring system (Kalyvas and David, 2004). The animals were placed on a metal grate and their walking ability was recorded. The scoring system is as follows: 0—no deficit; 1—limp tail only; 2—hind limb paresis but without leg dragging; 3—partial hind limb weakness with one or both legs dragging; 4—complete hind limb paralysis; 5—moribund, paralysis in hind limbs and possibly in one forelimb. The animals were monitored and assessed three times during the first week and then assessed daily for the remainder of the study.

Example

Hydralazine Treatment

A solution of hydralazine hydrochloride (Sigma) was prepared with phosphate buffered saline. The solution was then sterilized through a filter and stored at 4° C. Hydralazine (1 mg/kg) was administered through daily with intraperitoneal injections from the day the MOG/CFA emulsion was administered until the end of the 30 day study period. For sham treatments, mice were administered saline intraperitoneally rather than the hydralazine solution. Blood pressures were monitored using a CODA 2 system (Kent Scientific Corp.).

Example

Detection of Acrolein-Lysine Adducts by Immunoblotting

Acrolein-lysine adducts in the tissue homogenate was measured using a Bio-Dot SF Microfiltration Apparatus (Bio-Rad, Hercules, Calif., USA), as previously described (Luo et al., 2005a; Shao et al., 2006; Hamann et al., 2008a). Briefly, the tissue was homogenized with TritonX-100 (3%), and the following anti-proteases were added: 2 mmol/L pefabloc, 15 lmol/L pepstatin A, 20 lg/mL aprotinin, and 25 lg/mL leupeptin. The solution was centrifuged to pellet large pieces of tissue and the supernatant was stored at −80° C. until transferred to a nitrocellulose membrane. The membrane was blocked for 1 h in blocking buffer (0.2% casein and 0.1% Tween 20 in PBS) and transferred to 1:1000 polyclonal rabbit anti-acrolein (in blocking buffer with 2% goat serum and 0.025% sodium azide) (Novus Biologicals) for 18 h at 4° C. Next, the membrane was washed in blocking buffer and then transferred to 1:10000 alkaline phosphatase conjugated goat anti-rabbit IgG. It was then washed in blocking buffer followed by 0.1% Tween 20 in Tris-buffered saline. The membrane was exposed to Bio-Rad Immuno-Star Substrate (Bio-Rad) and visualized by chemiluminescence.

The optical density of bands was evaluated using Image J (NIH) and statistical comparison was performed with SAS 9.2 (SAS institute). Specifically, equal areas of each individual immunoblottied band of both anti-acrolein and anti-actin samples were selected and corresponding optical densities were obtained using Image J. The optical densities obtained from the anti-acrolein samples were standardized by their corresponding anti-actin samples before proceeding to statistical analysis. A Bicinchoninic acid (BCA) protein assay was also performed before the experiment to ensure equal loading of the samples.

Example

Immunofluorescence Imaging

Mice were perfusion fixed with 4% paraformaldehyde and the vertebral columns were removed and fixed in 4% paraformaldehyde overnight. Spinal cord tissues were extracted out of the vertebral column, cut into 1 cm pieces, and further fixed in 4% paraformaldehyde for 24-48 hours. The samples were cryoprotected by incubating for 24 h in a 10% sucrose solution, followed by 24 hours in a 20% sucrose solution. The samples were then imbedded in Tissue-Tek OCT compound (VWR, Batavia, Ill.) and frozen in liquid nitrogen. 15 μm sections were cut using a cryostat and mounted on gelatin coated slides. Sections were incubated with 5% goat serum and 0.5% Triton-X100 in phosphate buffered saline (PBS) for 30 minutes as blocking agents. After washing 3 times with PBS for 5 minutes, the sections were incubated in primary antibody for 1 hour at room temperature (RT). The sections were washed again for an additional 10 minutes and then incubated in secondary antibody for 1 hour at RT. After 15 minutes wash the sections were labeled by FluoroMyelin™ Red fluorescent myelin stain (Invitrogen, CA) for 30 minutes and washed. All sections were observed by fluorescence microscopy.

For quantification, the thoracic sections were imaged, and Adobe Photoshop was used to outline the demyelination area and total white matter area. Pixel area for each sample was calculated and the percentage of demyelination was obtained by dividing the total demyelinated area by total white matter area. Averages were obtained of the percent demyelination in 3 thoracic cross-sections for each animal. For each of the 3 groups, (control, EAE, EAE+HZ), 3 animals were used for immunofluorescence quantification.

Example

Immunoblotting shows increased acrolein-lysine adduct level in EAE mice spinal cord The acrolein-lysine adducts in control (n=3), EAE mice (n=3) and EAE+HZ mice (n=3) spinal cord are detected using Bio-Dot SF Microfiltration Apparatus. Loading controls are performed by Western blot using anti-actin antibody. Band intensities are analyzed using ImageJ (NIH) and are expressed in arbitrary units. Immunoblotting demonstrated that the acrolein-lysine adduct level in EAE mice spinal cord (20.27±3.0 a.u.) was significantly higher (p<0.05) than control (12.30±1.3 a.u., p<0.05). The acrolein-lysine adduct in EAE mice spinal cord treated with hydralazine was comparable with the undiseased control at 15.14±1.6 a.u. One way ANOVA and post hoc tests were used for statistical analysis. All data are expressed as mean±SEM.

Example

Figure 2:
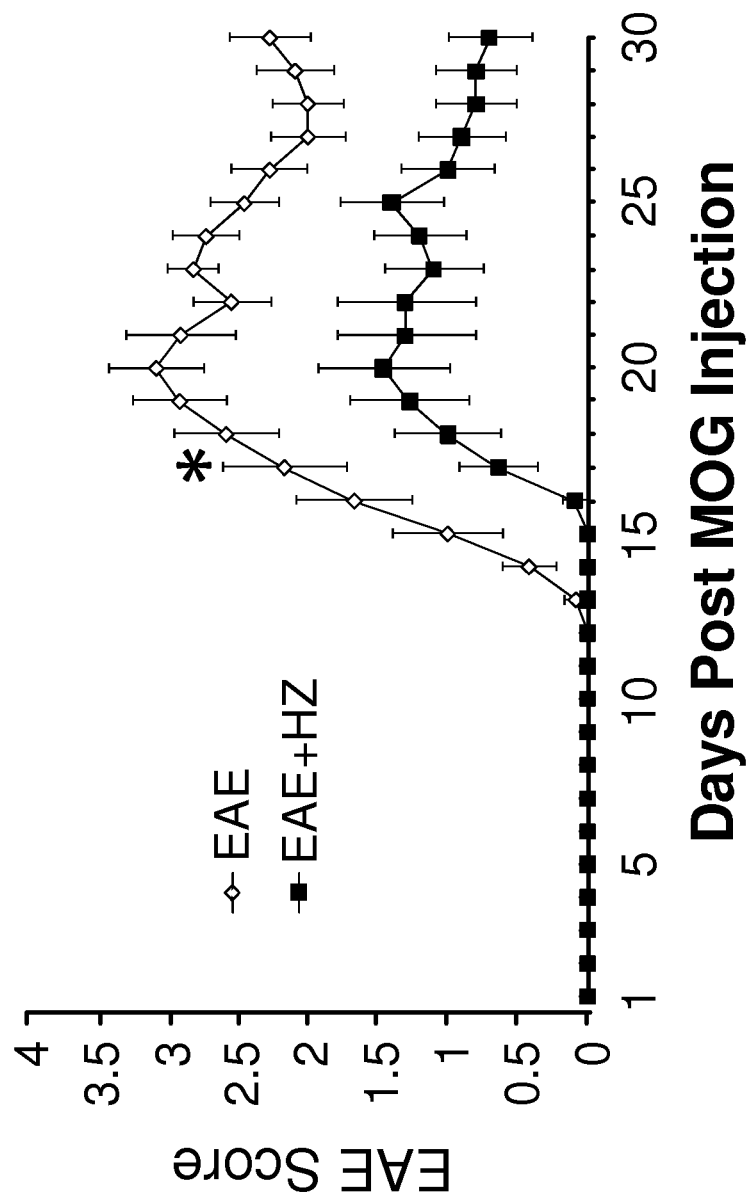
FIG. 2A shows a comparison of behavioral score in each day between hydralazine treated (EAE+HZ) and sham treated (EAE) groups in EAE mice.
FIG. 2B shows a comparison of the onset of symptoms between hydralazine treated (EAE+HZ) and sham treated (EAE) groups.
FIG. 2C shows a quantitative comparison of mean behavioral score between hydralazine treated (EAE+HZ) and sham treated (EAE) groups.
Figure 2:
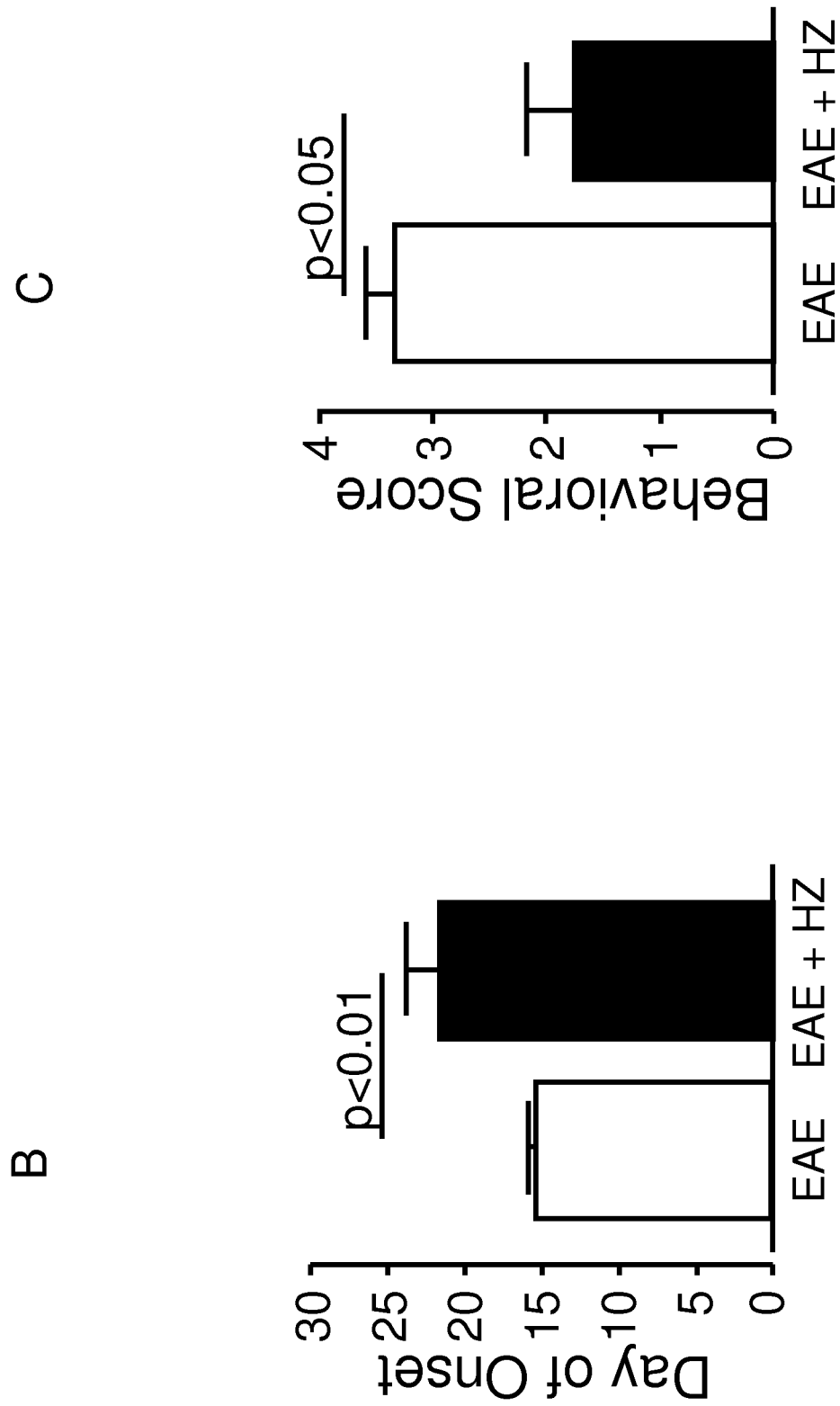

Hydralazine Delayed the Onset of EAE Mice Symptoms and Reduced the Severity of the Paralysis One group of EAE mice are injected with hydralazine (EAE+HZ) at the dose of 1 mg/kg daily starting from the day of induction (n=11). In the sham-treated group (EAE), an equal amount of saline is injected daily (n=12). Both hydralazine and saline (sham) treatments are carried out for 30 days post induction. The behavioral scores of the two groups of mice are recorded daily (FIG. 2A). All the mice in EAE group showed symptoms of motor impairment as evaluated with the 5-point behavioral test. Nine of 11 mice in the treated group developed behavioral deficits. However, the behavioral deficits in treated group emerged significantly later than in sham-treated group. The average onset of symptoms for the hydralazine treated group was 21.73±2.1 days post induction, which was significantly longer (p<0.01), than the sham (EAE) group (15.42±0.4 days post emulsion injection), as shown in FIG. 2B. The onset of symptoms for the 2 mice that did not develop behavioral deficits is considered to be at least 30 days post induction. In addition to onset, the severity of the symptoms in the hydralazine treated group was significantly lower than the sham group at each daily evaluation starting from 17 days post induction (p<0.01, FIG. 2A). When the highest score for each mouse is taken and averaged within each group, the hydralazine treated group showed a significantly lower (p<0.05) average behavioral score (1.72±0.4) than the EAE group (3.33±0.3), as shown in FIG. 2C. No serious hypotension was detected following the treatment of hydralazine in both normal and EAE mice. Specifically, the average systolic pressure of normal mice are 125.6±3.6 mmHg (no hydralazine) and 118.5±6.4 mmHg (with hydralazine) (n=4, p>0.05). The average systolic pressure of EAE mice are 153.9±5.0 mmHg (no hydralazine) and 134.8±4.5 mmHg (with hydralazine) (n=3, p>0.05).

FIG. 2A shows a comparison of behavioral score in each day between hydralazine treated (EAE+HZ) and sham treated (EAE) groups in EAE mice. The hydralazine treated group shows a significant improvement (p<0.01) for comparison between the EAE+HZ and EAE groups after Day 17. FIG. 2B shows a comparison of the onset of symptoms between hydralazine treated (EAE+HZ) and sham treated (EAE) groups. The hydralazine treated group shows a significant improvement (p<0.01). FIG. 2C shows a quantitative comparison of mean behavioral score between hydralazine treated (EAE+HZ) and sham treated (EAE) groups. The hydralazine treated group shows a significant improvement (p<0.05). The highest score for each mouse was taken and averaged within each group. All data are expressed as mean±SEM.

Example

Improvement of Behavioral Outcome Through Acrolein Trapping by Hydralazine when Initiated Following the Emergence of Motor Deficits FIG. 1A shows the behavioral scores evaluated daily on a 5 point scale for mice in sham treated (EAE) and hydralazine treated (EAE+HZ) groups. The hydralazine treated group shows significant differences (p<0.05) for all comparisons following day 2 of the treatment. For each animal, behavioral tests are conducted and displayed starting at day 0, where treatment is started at day 1 which is determined based on the first appearance of behavioral deficits. Animals in the EAE group receive saline injections, while EAE+HZ mice receive saline containing hydralazine at 1 mg/kg. The comparison indicates that differences between the treatment groups become apparent on day 2 and the positive effect of hydralazine on motor function remains significant throughout the experimental period. FIG. 1B shows that when the highest scores for each mouse are averaged within the group, the mean score of behavioral deficits is significantly decreased (p<0.05) in the EAE+HZ group compared to the EAE mice demonstrating a significant reduction in symptom severity. N=8 in each group. All data are expressed as mean±SEM.

Example

Figure 3:
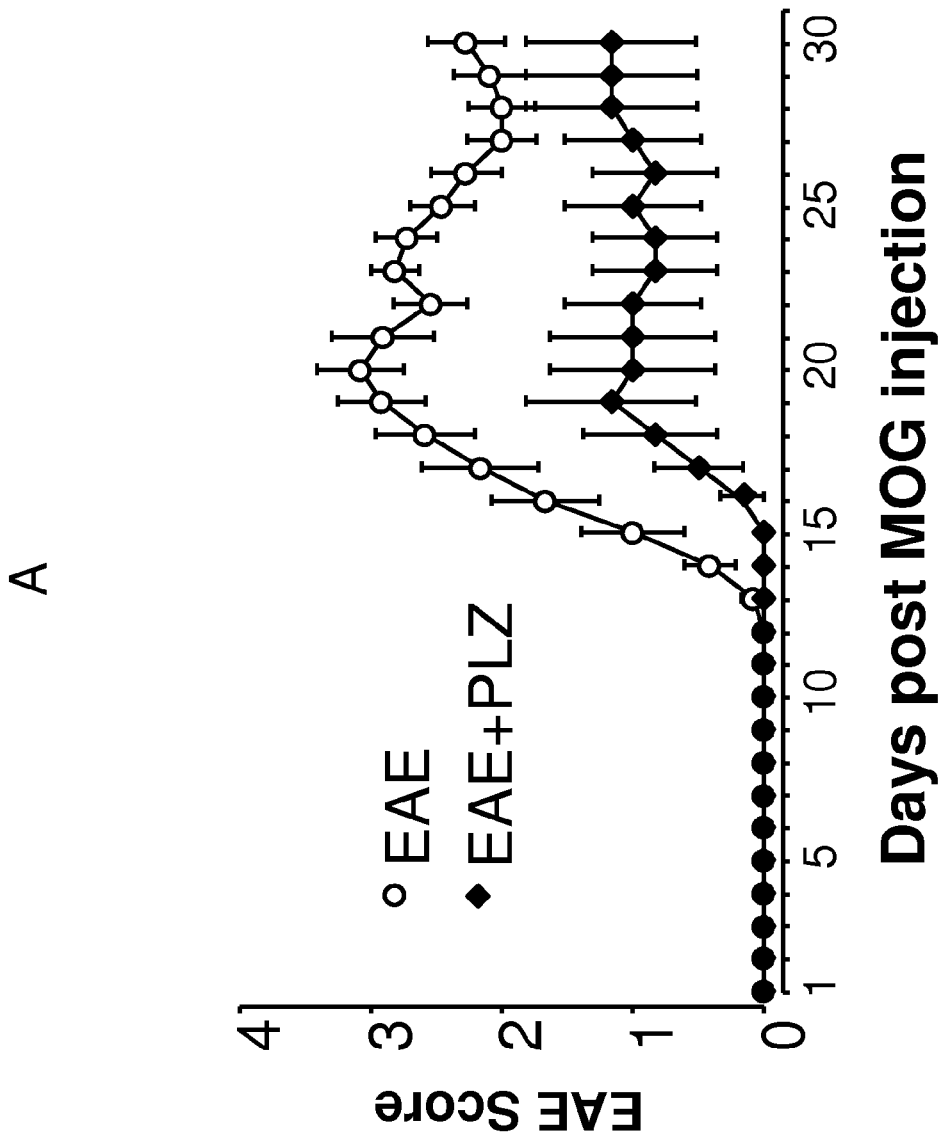
FIG. 3A shows the behavioral scores evaluated daily on a 5 point scale for mice in a sham treated (EAE) compared to a phenelzine treated (EAE+PLZ) groups.
FIG. 3B shows a comparison of the time to EAE symptom onset between sham treated (EAE) compared to a phenelzine treated (PLZ) groups.
FIG. 3C shows mean behavioral scores are significantly increased in EAE mice compared to the phenelzine treated (EAE+PLZ) group (p<0.005).
Figure 3:
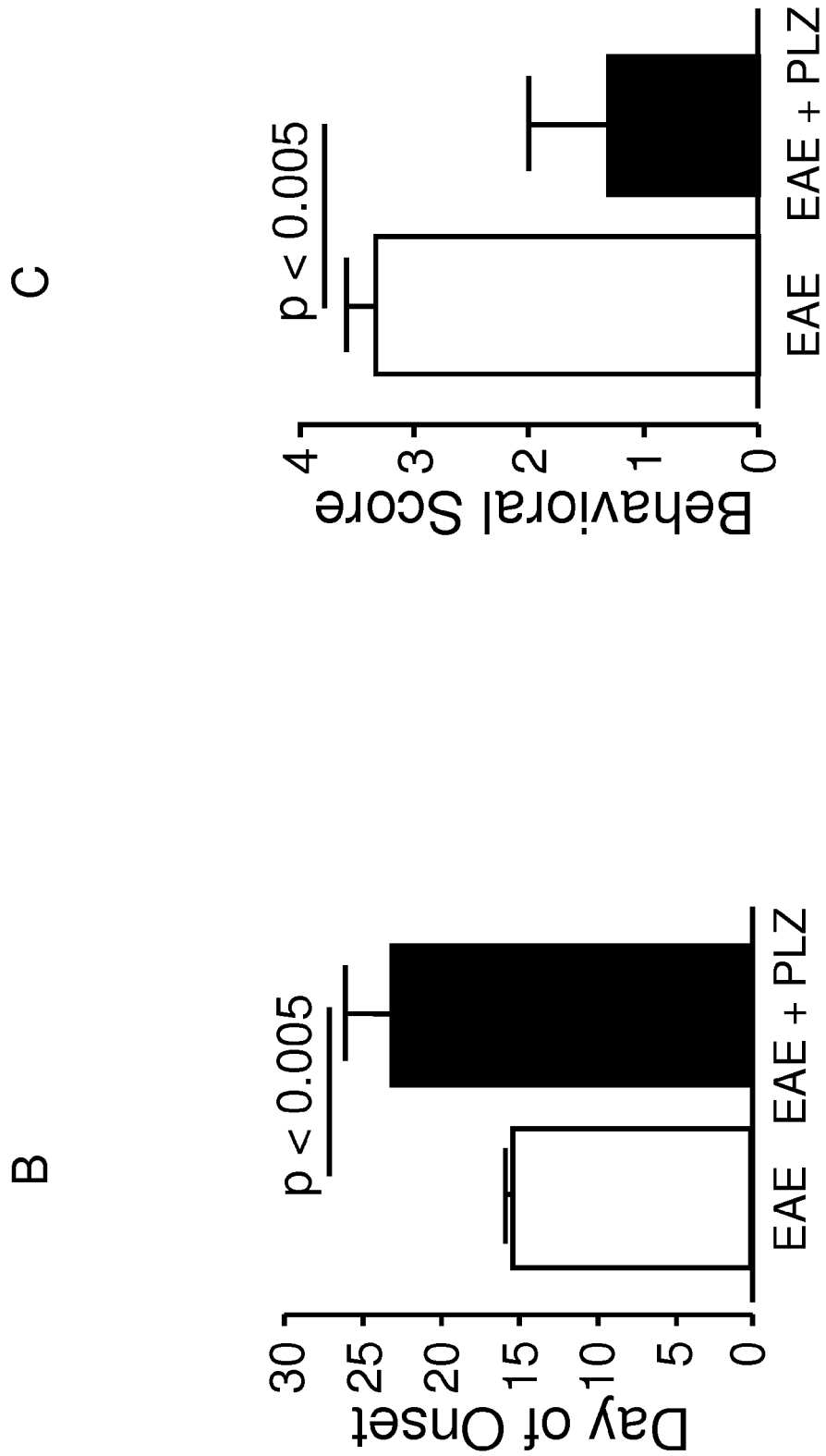

Improvement of Behavioral Outcome Through Acrolein Trapping by Phenelzine in EAE Mice FIG. 3A shows the behavioral scores evaluated daily on a 5 point scale for mice in a sham treated (EAE) compared to a phenelzine treated (EAE+PLZ) groups. The phenelzine treated group shows significant differences for all comparisons following day 14. Phenelzine is administered via intraperitoneal (IP) injections at 15 mg/kg for 30 days. FIG. 3B shows a comparison of the time to EAE symptom onset between sham treated (EAE) compared to a phenelzine treated (PLZ) groups. The phenelzine treated (EAE+PLZ) group show a significant delay in disease progression (p<0.005). FIG. 3C shows mean behavioral scores are significantly increased in EAE mice compared to the phenelzine treated (EAE+PLZ) group (p<0.005). The highest score for each mouse was taken and averaged within each group. All data are expressed as mean±SEM. The data support the conclusion that a significant decrease in both disease progression and of symptom severity at all time point is observed with treatment using the compounds, compositions, methods, and dosage forms described herein.

Example

Figure 4:
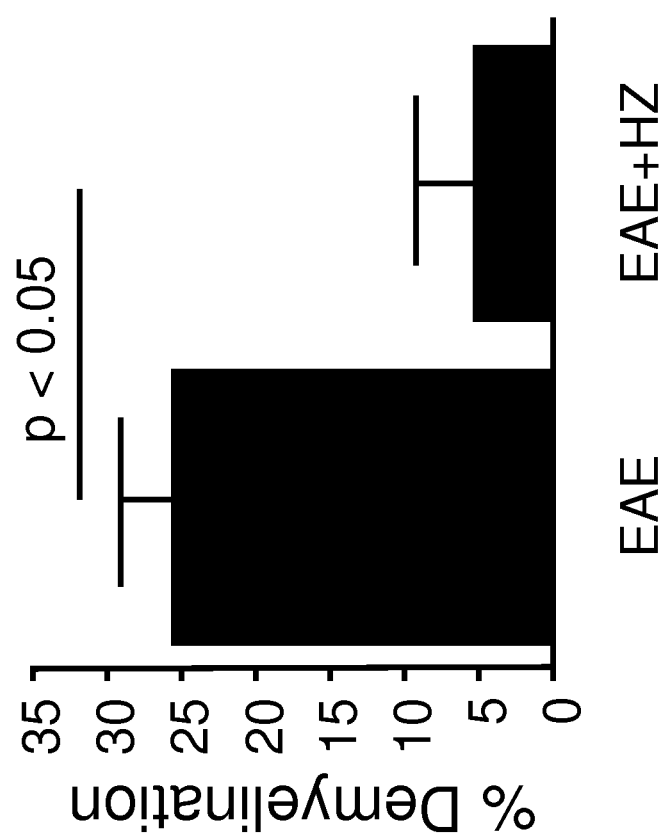
FIG. 4 shows a comparison of percent demyelination on spinal cord cross section between hydralazine treated (EAE+HZ) and sham treated (EAE) groups in EAE mice.

Hydralazine Treatment Lessens the Demyelination Area on Spinal Cord Cross Section The thoracic segment of spinal cord samples harvested from Control, hydralazine treated (EAE+HZ), and sham treated mice (EAE) were cut in 15 µm cross sections and labeled with NF200 (to stain axons green) and fluoromyelin (to stain myelin red). Total white matter area and lesion areas are manually outlined and the pixel area is calculated. Percent demyelination is calculated by dividing total demyelinated area by total white matter area. Control sections showed no signs of demyelination or axonal loss. Sections taken from EAE mice show demyelinated lesions and axonal loss. Sections taken from EAE mice treated with hydralazine show substantially fewer demyelinating lesions and axonal loss, compared to untreated EAE mice sections. The percent of demyelination in white matter is compared between EAE and EAE+HZ groups. The hydralazine treatment significantly decreases ($p<0.05$) demyelination area from $25.58\pm3.8\%$ (sham treated) to $5.10\pm4.2\%$ (hydralazine treated) (n=3, FIG. 4).

Without being bound by theory, it is believed herein that acrolein-mediated pathology in MS may be mediated through multiple mechanisms. For example, acrolein may break down the myelin sheath by attacking lipids and proteins, the main components of myelin (Morell and Quarles, 1999). However, acrolein pathogenesis may also lead to enzymatic damage of myelin (Shields and Banik, 1999; Shields et al., 1999). The reduction of EAE induced demyelination in spinal cord by anti-acrolein treatment may be consistent with a causal role of acrolein in myelin damage.

Without being bound by theory, it is believed herein that acrolein may also contribute directly to axonal degeneration, another major MS pathology (Trapp et al., 1998; Trapp et al., 1999; Trapp and Nave, 2008). Without being bound by theory, it is believed that pathogenesis is due to acrolein compromising the axonal membrane and consequently triggering axonal degeneration (Shi et al., 2002; Luo and Shi, 2004). Such axonal damage can be further exacerbated through acrolein-mediated oxidative stress and mitochondrial dysfunction (Adams and Klaidman, 1993; Luo et al., 2005b; Luo and Shi, 2005). Therefore, described herein are methods, uses, formulations, and unit dosage forms that include anti-acrolein treatment that may reduce both acrolein-mediated myelin damage as well as acrolein-mediated axonal damage. Taken together, acrolein is likely a major factor in MS that contributes to multiple mechanisms of demyelination, axonal degeneration, and functional loss.

Without being bound by theory, it is believed herein that the therapeutic effect of the compounds, compositions, methods, and uses described herein is attributable at least in part to the trapping of acrolein in vivo. In contrast, though without being bound by theory, it is also believed herein that the therapeutic effect of the compounds, compositions, methods, and uses described herein is not primarily attributable the simple superoxide scavenging. It has been discovered herein that hydralazine is not an effective superoxide scavenger, and therefore it does not appear that hydralazine is a non-specific free radical scavenger. It has been reported that superoxide scavenger and non-specific free radical scavengers are not generally effective in MS treatment. (Hamann et al., 2008a).

The following publications, and each additional publication cited herein, are incorporated herein by reference in their entirety.

Adams J D, Jr., Klaidman L K (1993) Acrolein-induced oxygen radical formation. Free Radical Biology & Medicine 15:187-193.

Burcham P C, Pyke S M (2006) Hydralazine inhibits rapid acrolein-induced protein oligomerization: role of aldehyde scavenging and adduct trapping in cross-link blocking and cytoprotection. Mol Pharmacol 69:1056-1065.

Burcham P C, Kerr P G, Fontaine F (2000) The antihypertensive hydralazine is an efficient scavenger of acrolein. Redox Rep 5:47-49.

Burcham P C, Kaminskas L M, Fontaine F R, Petersen D R, Pyke S M (2002) Aldehyde-sequestering drugs: tools for studying protein damage by lipid peroxidation products. Toxicology 181-182:229-236.

Burcham P C, Fontaine F R, Kaminskas L M, Petersen D R, Pyke S M (2004) Protein adduct-trapping by hydrazinophthalazine drugs: mechanisms of cytoprotection against acrolein-mediated toxicity. Mol Pharmacol 65:655-664.

Compston A, Coles A (2008) Multiple sclerosis. Lancet 372:1502-1517.

Esterbauer H, Schaur R J, Zollner H (1991) Chemistry and biochemistry of 4-hydroxynonenal, malonaldehyde and related aldehydes. Free Radical Biology & Medicine 11:81-128.

Ghilarducci D P, Tjeerdema R S (1995) Fate and effects of acrolein. Rev Environ Contam Toxicol 144:95-146.

Gilgun-Sherki Y, Melamed E, Offen D (2004) The role of oxidative stress in the pathogenesis of multiple sclerosis: the need for effective antioxidant therapy. J Neurol 251:261-268.

Gold R, Linington C, Lassmann H (2006) Understanding pathogenesis and therapy of multiple sclerosis via animal models: 70 years of merits and culprits in experimental autoimmune encephalomyelitis research. Brain 129:1953-1971.

Halliwell B, Gutteridge J M C (1999) Free radicals in biology and medicine. Oxford: Oxford University Press.

Hamann K, Shi R (2009) Acrolein scavenging: a potential novel mechanism of attenuating oxidative stress following spinal cord injury. J Neurochem 111:1348-1356.

Hamann K, Nehrt G, Ouyang H, Duerstock B, Shi R (2008a) Hydralazine inhibits compression and acrolein-mediated injuries in ex vivo spinal cord. J Neurochem 104:708-718.

Hamann K, Durkes A, Ouyang H, Uchida K, Pond A, Shi R (2008b) Critical role of acrolein in secondary injury following ex vivo spinal cord trauma. J Neurochem 107:712-721.

Kalyvas A, David S (2004) Cytosolic phospholipase A2 plays a key role in the pathogenesis of multiple sclerosis-like disease. Neuron 41:323-335.

Kaminskas L M, Pyke S M, Burcham P C (2004a) Reactivity of hydrazinophthalazine drugs with the lipid peroxidation products acrolein and crotonaldehyde. Org Biomol Chem 2:2578-2584.

Kaminskas L M, Pyke S M, Burcham P C (2004b) Strong protein adduct trapping accompanies abolition of acrolein-mediated hepatotoxicity by hydralazine in mice. J Pharmacol Exp Ther 310:1003-1010.

Kehrer J P, Biswal S S (2000) The molecular effects of acrolein. Toxicological Sciences 57:6-15.

Liu-Snyder P, McNally H, Shi R, Borgens R B (2006) Acrolein-mediated mechanisms of neuronal death. J Neurosci Res 84:209-218.

Lovell M A, Xie C, Markesbery W R (2001) Acrolein is increased in Alzheimer's disease brain and is toxic to primary hippocampal cultures. Neurobiology of Aging 22:187-194.

Luo J, Shi R (2004) Acrolein induces axolemmal disruption, oxidative stress, and mitochondrial impairment in spinal cord tissue. Neurochemistry International 44:475-486.

Luo J, Shi R (2005) Acrolein induces oxidative stress in brain mitochondria. Neurochem Int 46:243-252.

Luo J, Uchida K, Shi R (2005a) Accumulation of acrolein-protein adducts after traumatic spinal cord injury. Neurochem Res 30:291-295.

Luo J, Robinson J P, Shi R (2005b) Acrolein-induced cell death in PC12 cells: role of mitochondria-mediated oxidative stress. Neurochem Int 47:449-457.

Montine T J, Neely M D, Quinn J F, Beal M F, Markesbery W R, Roberts L J, Morrow J D (2002) Lipid peroxidation in aging brain and Alzheimer's disease. Free Radic Biol Med 33:620-626.

Morell P, Quarles R H (1999) In: Basic Neurochemistry: Molecular, Cellular, and Medical Aspects (Siegel G J, Agranoff B W, Alberts R W, Molinoff P B, eds). Philadelphia: Lippincott Williams & Wilkins.

Shao B, O'Brien K D, McDonald T O, Fu X, Oram J F, Uchida K, Heinecke J W (2005a) Acrolein modifies apolipoprotein A-I in the human artery wall. Ann NY Acad Sci 1043:396-403.

Shao B, Fu X, McDonald T O, Green P S, Uchida K, O'Brien K D, Oram J F, Heinecke J W (2005b) Acrolein impairs ATP binding cassette transporter A1-dependent cholesterol export from cells through site-specific modification of apolipoprotein A-I. J Biol Chem 280:36386-36396.

Shao C, Roberts K N, Markesbery W R, Scheff S W, Lovell M A (2006) Oxidative stress in head trauma in aging. Free Radic Biol Med 41:77-85.

Shi R, Luo J, Peasley M A (2002) Acrolein inflicts axonal membrane disruption and conduction loss in isolated guinea pig spinal cord. Neuroscience 115:337-340.

Shibata N, Nagai R, Miyata S, Jono T, Horiuchi S, Hirano A, Kato S, Sasaki S, Asayama K, Kobayashi M (2000) Non-oxidative protein glycation is implicated in familial amyotrophic lateral sclerosis with superoxide dismutase-1 mutation. Acta Neuropathol (Berl) 100:275-284.

Shields D C, Banik N L (1999) Pathophysiological role of calpain in experimental demyelination. J Neurosci Res 55:533-541.

Shields D C, Schaecher K E, Saido T C, Banik N L (1999) A putative mechanism of demyelination in multiple sclerosis by a proteolytic enzyme, calpain. Proc Natl Acad Sci USA 96:11486-11491.

Smith K J, Kapoor R, Felts P A (1999) Demyelination: the role of reactive oxygen and nitrogen species. Brain Pathol 9:69-92.

Trapp B D, Nave K A (2008) Multiple sclerosis: an immune or neurodegenerative disorder? Annu Rev Neurosci 31:247-269.

Trapp B D, Ransohoff R, Rudick R (1999) Axonal pathology in multiple sclerosis: relationship to neurologic disability. Curr Opin Neurol 12:295-302.

Trapp B D, Peterson J, Ransohoff R M, Rudick R, Mork S, Bo L (1998) Axonal transection in the lesions of multiple sclerosis. N Engl J Med 338:278-285.

Uchida K, Kanematsu M, Morimitsu Y, Osawa T, Noguchi N, Niki E (1998a) Acrolein is a product of lipid peroxidation reaction. Formation of free acrolein and its conjugate with lysine residues in oxidized low density lipoproteins. J Biol Chem 273:16058-16066.

Uchida K, Kanematsu M, Sakai K, Matsuda T, Hattori N, Mizuno Y, Suzuki D, Miyata T, Noguchi N, Niki E, Osawa T (1998b) Protein-bound acrolein: potential markers for oxidative stress. Proceedings of the National Academy of Sciences of the United States of America 95:4882-4887.

Wood P L, Khan M A, Moskal J R, Todd K G, Tanay V A, Baker G (2006) Aldehyde load in ischemia-reperfusion brain injury: neuroprotection by neutralization of reactive aldehydes with phenelzine. Brain Res 1122:184-190.

What is claimed is:

1. A method for treating a patient with multiple sclerosis, the method comprising the step of administering to the patient a therapeutically effective amount of one or more fused hydrazinopyridazines.

2. The method of claim 1 wherein at least one phenylethylhydrazine is a compound of the formula

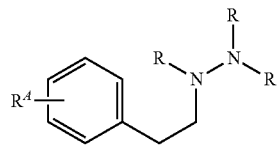

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

3. The method of claim 1 wherein at least one fused hydrazinopyridazine is a compound of the formula

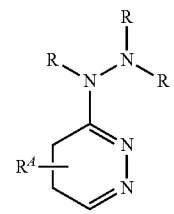

or a pharmaceutically acceptable salt thereof, wherein:

R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and $R^A$ represents three substituents, one of which is selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfonyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and two of $R^A$ are taken together with the attached carbons to form an optionally substituted saturated, unsaturated, or aromatic carbocycle or heterocycle.

4. The method of claim 2 wherein $R^A$ represents three hydrogen; or
$R^A$ includes an optionally substituted benzo group; or
$R^A$ includes an optionally substituted fused piperidine; or
$R^A$ includes a hydrazino or derivative thereof; or
$R^A$ includes a hydrazino; or
$R^A$ includes amino or a derivative thereof; or
$R^A$ includes dialkylamino, where each alkyl is independently selected, and independently optionally substituted.

5. The method of claim 3 wherein $R^A$ represents a hydrogen; or
$R^A$ includes an optionally substituted benzo group; or
$R^A$ includes an optionally substituted fused piperidine; or
$R^A$ includes a hydrazino or derivative thereof; or
$R^A$ includes a hydrazino; or
$R^A$ includes amino or a derivative thereof; or
$R^A$ includes dialkylamino, where each alkyl is independently selected, and independently optionally substituted.

6. The method of claim 4 wherein each R is hydrogen.
7. The method of claim 4 wherein at least one R is acyl.
8. The method of claim 4 wherein at least one R is optionally substituted alkoxycarbonyl.
9. The method of any claim 2 wherein each R is hydrogen; or at least one R is acyl; or at least one R is optionally substituted alkoxycarbonyl.
10. The method of claim 3 wherein each R is hydrogen; or at least one R is acyl; or at least one R is optionally substituted alkoxycarbonyl.
11. The method of claim 5 wherein each R is hydrogen.
12. The method of claim 5 wherein at least one R is acyl.
13. The method of claim 5 wherein at least one R is optionally substituted alkoxycarbonyl.
14. The method of claim 1 wherein the fused hydrazinopyridazine, is selected from the group consisting of hydralazine, dihydralazine, and endralazine.
15. A unit dosage form for treating multiple sclerosis, the unit dosage form comprising a therapeutically effective amount of one or more fused hydrazinopyridazines, pharmaceutically acceptable salts thereof, or combinations thereof, in a single or divided format.
16. The unit dosage form of claim 15 wherein at least one phenylethylhydrazine is a compound of the formula

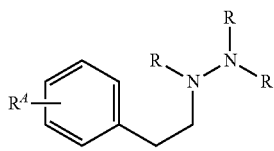

or a pharmaceutically acceptable salt thereof, wherein:
R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and
$R^A$ represents three substituents selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; or two of $R^A$ are taken together with the attached carbons to form an optionally substituted saturated, unsaturated, or aromatic carbocycle or heterocycle.

17. The unit dosage form of claim 15 wherein at least one fused hydrazinopyridazine is a compound of the formula

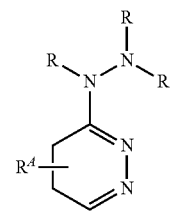

or a pharmaceutically acceptable salt thereof, wherein:
R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and
$R^A$ represents three substituents, one of which is selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfinyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and two of $R^A$ are taken together with the attached carbons to form an optionally substituted saturated, unsaturated, or aromatic carbocycle or heterocycle.

18. The unit dosage form of claim 15 wherein the fused hydrazinopyridazine, is selected from the group consisting of hydralazine, dihydralazine, and endralazine.
19. The unit dosage form of claim 15 wherein the fused hydrazinopyridazine, is included at a dose that is not therapeutically effective or clinically effective for treating hypertension, in a single or divided format.
20. The unit dosage form of claim 15 wherein the fused hydrazinopyridazine is included at a dose that is not therapeutically effective or clinically effective for treating depression, in a single or divided format.
21. The unit dosage form of claim 15 wherein the fused hydrazinopyridazine is included at a dose that is not therapeutically effective or clinically effective for treating anxiety, in a single or divided format.
22. A composition comprising a fused hydrazinopyridazines in a therapeutically effective amount for treating a patient with multiple sclerosis.
23. The composition of claim 22 wherein at least one fused hydrazinopyridazine is a compound of the formula

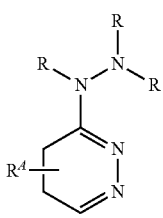

or a pharmaceutically acceptable salt thereof, wherein:
R is independently selected in each instance from hydrogen, acyl, or sulfonyl; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and
$R^A$ represents three substituents, one of which is selected from the group consisting of hydrogen, halo, hydroxy and derivatives thereof, amino and derivatives thereof, thio and derivatives thereof, acyl, carboxylate or a derivative thereof, hydroxylamino and derivatives thereof, hydrazino and derivatives thereof, sulfonyl or a derivative thereof, or sulfonyl or a derivative thereof; or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and two of $R^A$ are taken together with the attached carbons to form an optionally substituted saturated, unsaturated, or aromatic carbocycle or heterocycle.

24. The composition of claim 23 wherein $R^A$ represents a hydrogen; or
$R^A$ includes an optionally substituted benzo group; or
$R^A$ includes an optionally substituted fused piperidine; or
$R^A$ includes a hydrazino or derivative thereof; or
$R^A$ includes a hydrazino; or
$R^A$ includes amino or a derivative thereof; or
$R^A$ includes dialkylamino, where each alkyl is independently selected, and independently optionally substituted.

25. The composition of claim 23 wherein each R is hydrogen; or at least one R is acyl; or at least one R is optionally substituted alkoxycarbonyl.

26. The composition of claim 25 wherein each R is hydrogen.

27. The composition of claim 25 wherein at least one R is acyl.

28. The composition of claim 25 wherein at least one R is optionally substituted alkoxycarbonyl.

29. The composition of claim 22 wherein the fused hydrazinopyridazine, is selected from the group consisting of hydralazine, dihydralazine, and endralazine.

* * * * *